United States Patent [19]

Longest et al.

[11] Patent Number: 5,588,068

[45] Date of Patent: *Dec. 24, 1996

[54] METHODS AND APPARATUS FOR INSPECTING THE APPEARANCE OF SUBSTANTIALLY CIRCULAR OBJECTS

[75] Inventors: H. Cary Longest, Midlothian; James L. Lynch, Richmond, both of Va.

[73] Assignee: Philip Morris Incorporated, New York, N.Y.

[*] Notice: The portion of the term of this patent subsequent to Dec. 4, 2012, has been disclaimed.

[21] Appl. No.: 315,643

[22] Filed: Sep. 30, 1994

Related U.S. Application Data

[63] Continuation-in-part of Ser. No. 985,875, Dec. 4, 1992, Pat. No. 5,353,357.

[51] Int. Cl.[6] .................................................. G06K 9/00
[52] U.S. Cl. .................... 382/141; 382/199; 348/92; 348/125; 356/237
[58] Field of Search .............................. 382/141, 143, 382/149, 266; 356/237, 445; 250/223 R; 209/536; 348/86, 125, 128

[56] References Cited

U.S. PATENT DOCUMENTS

| | | | |
|---|---|---|---|
| 3,818,223 | 6/1974 | Gibson et al. | 356/237 |
| 4,606,635 | 8/1986 | Miyazawa et al. | 356/240 |
| 4,969,746 | 11/1990 | McConnell et al. | 356/237 |
| 4,972,494 | 11/1990 | White et al. | 382/143 |
| 4,976,544 | 12/1990 | Neri | 356/237 |
| 5,127,737 | 7/1992 | Neri | 356/237 |
| 5,432,600 | 7/1995 | Grollimund et al. | 356/237 |

*Primary Examiner*—Leo Boudreau
*Assistant Examiner*—David R. Anderson
*Attorney, Agent, or Firm*—Charles E. B. Glenn; James E. Schardt; Kevin B. Osborne

[57] ABSTRACT

Substantially circular objects such as the ends of the filters of filter tipped cigarettes are inspected for acceptable appearance utilizing a blob analysis which includes imaging a peripheral region so as to provide resolution along the edge of the circular object.

40 Claims, 11 Drawing Sheets

Fig. 3
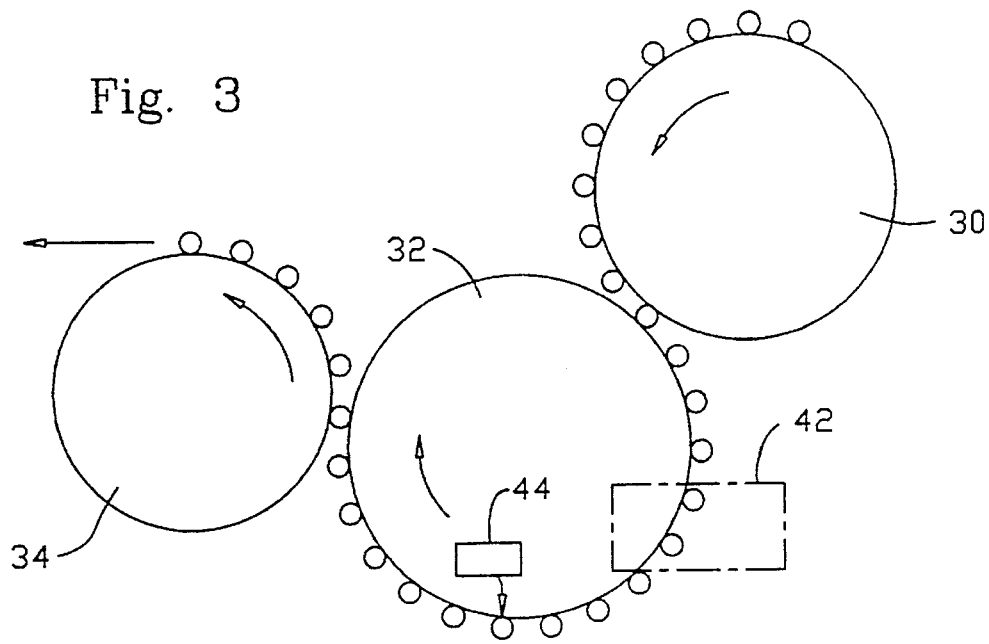
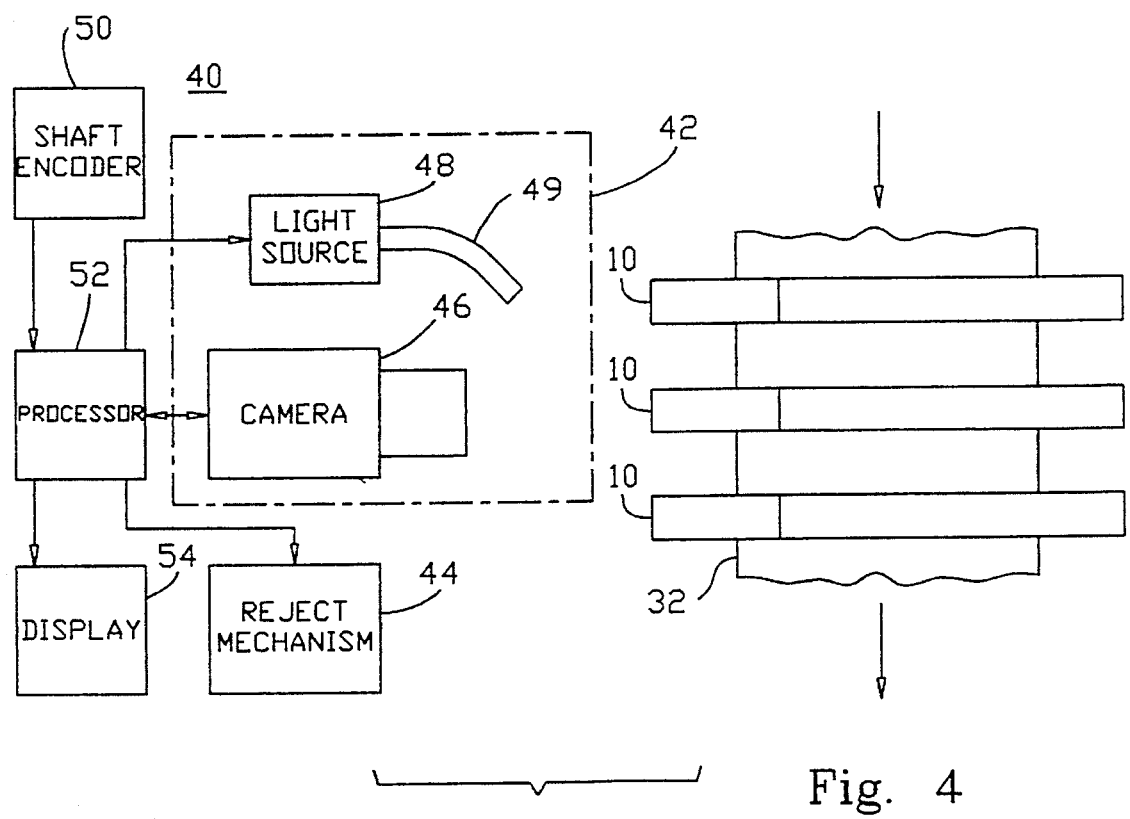
Fig. 4

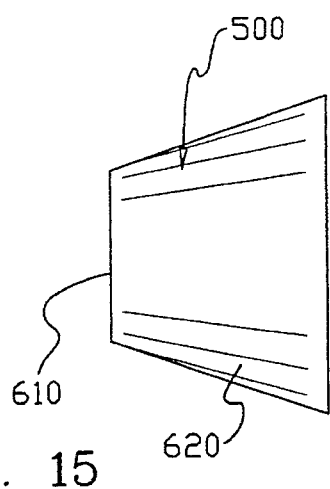
Fig. 15
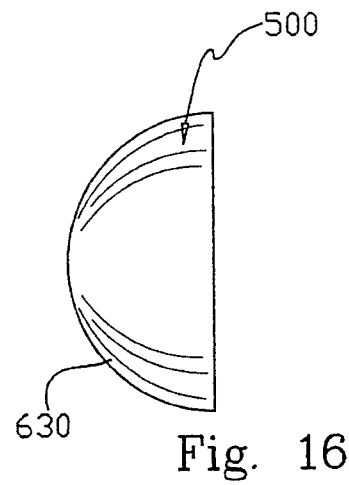
Fig. 16
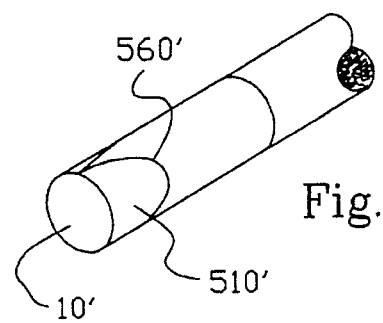
Fig. 19
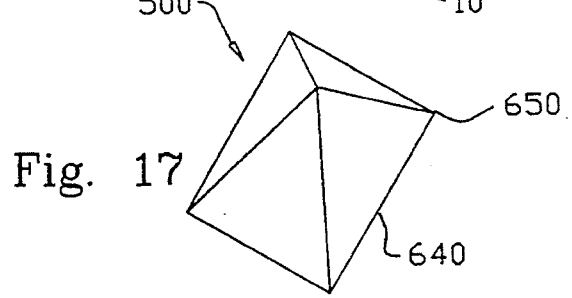
Fig. 17
Fig. 20
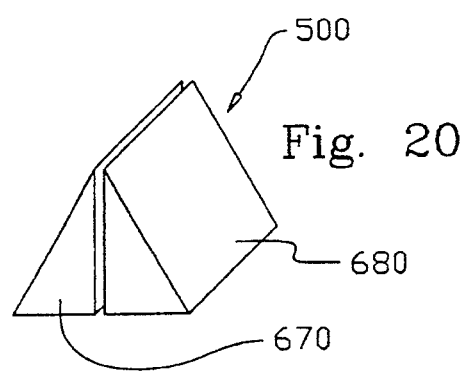
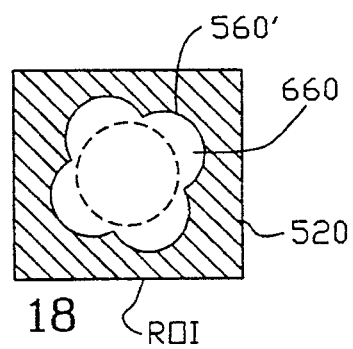
Fig. 18
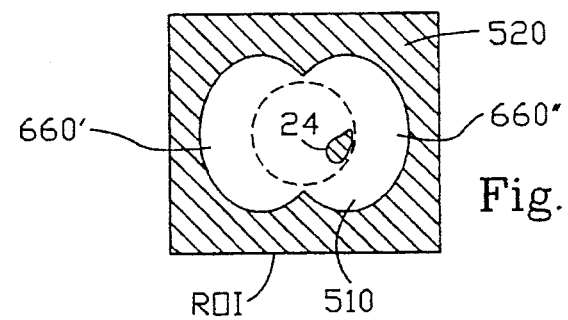
Fig. 21

METHODS AND APPARATUS FOR INSPECTING THE APPEARANCE OF SUBSTANTIALLY CIRCULAR OBJECTS

CROSS-REFERENCE

The present application is a continuation-in-part of commonly assigned U.S. Ser. No. 07/985,875, filed Dec. 4, 1992 now U.S. Pat. No. 5,353,357.

FIELD OF INVENTION

The present invention relates to methods and apparatus for inspecting the appearance of substantially circular objects such as the ends of cigarettes or cigarette components.

BACKGROUND OF THE INVENTION

Modern manufacturing equipment is capable of producing products at very high speeds. For example, it is not at all uncommon for modern cigarette making equipment to produce cigarettes at the rate of 5000–6000 per minute, and speeds as high as 12,000 per minute are also achievable. It is, of course, desirable to inspect the appearance of products to the greatest possible extent. Abnormal appearance in itself may be a reason for rejecting a product. Moreover, abnormal appearance may indicate an underlying structural defect which may be another reason why the product should be rejected. In addition to facilitating rejection of defective products, appearance inspection may be used to identify what types of defects might be occurring so that the production equipment can be adjusted to reduce the occurrence of such defects.

In general, a more complete the inspection of products is preferred, including, if possible, an inspection of the full image of to each product, rather than just an inspection of portions of each image or an inspection of only a presumably representative sample of product images. Also, the more current the results of the inspection the better, so that when a succession of defective products is detected, prompt corrective action can be undertaken to minimize the production of products with the defect.

The foregoing considerations become compounded and more critical at elevated production speeds, where high speed equipment tends to be more sensitive to misadjustments, poor maintenance and/or improper operation. The need for immediate detection of defects is also more critical with high speed equipment, because massive quantities of defective products can be produced in just a short time. Defects must be detected promptly, and the equipment either stopped or adjusted to eliminate the cause of the defects.

During the manufacture of cigarettes, various types of defects may appear at their circular end face of the filter or at other substantially circular surfaces.

Although most cigarettes are circular in cross-section, some cigarettes are oval. It will be readily apparent to those skilled in the art how the principles of the present invention can be adapted to oval cigarettes. Because oval objects are sufficiently like circular objects for purposes of the present invention, all such objects will be referred to herein as circular or substantially circular.

Among the defects which might appear at the circular end surfaces of cigarettes are the following: (1) an absence of a intended component such as a filter; (2) an improper size (i.e., it is either too large or too small); (3) an improper shape (e.g., not sufficiently circular); (4) an improper sealing of a wrapper (e.g., a "flag" appears on the plug wrap (the paper wrapper around a filter component) or a "flag" appears on the tipping paper (the wrapper which joins the filter to the tobacco rod)); (5) a gap appears between the plug wrap and the underlying filter material (a so-called "by-pass") or between the tipping paper and the underlying filter plug (another form of by-pass); or (6) a discoloration at the filter end surface (e.g., in the case of charcoal filters, when one or more particles of charcoal has located on the end surface of the filter (so-called "black eyes")).

In view of the foregoing, it is an object of the present invention to provide methods and apparatus for inspecting the appearance of substantially circular objects such as the ends of cigarettes for one or more defects of the type described above.

It is another object of this invention to provide methods and apparatus for inspecting the appearance of substantially circular objects such as the ends of cigarettes at the extremely high speeds at which such articles are typically made in modern manufacturing equipment.

SUMMARY OF THE INVENTION

These and other objects of the invention are accomplished in accordance with the present invention by forming a video image of each substantially circular object to be inspected. Preferably the substantially circular object is supported so that it visually contrasts with its background in the video image. In the case of inspection of the substantially circular end of a cigarette or a cigarette component, for example, the item may be supported so that the end to be inspected is located away from the supporting structure. Preferably, the cigarette or end of the cigarette or component is illuminated obliquely so that little or no illumination falls on the adjacent portion of the supporting structure. The end of the component therefore tends to appear light or white against a dark or black background in the resulting video image. To further enhance contrast, the adjacent surfaces of the support structure is preferably light absorbing (e.g., dark in color) and/or non-reflective.

The above-described video image is scanned and digitized to produce a digital, grey scale image. If the substantially circular object does not fill the entire field of view of the video image forming component (e.g., a video camera), then preferably only that portion of the camera screen containing the object image is scanned so as to increase the speed at which successive images can be captured. Alternatively or in addition, where the substantially circular object does not fill the entire field of view of the video camera, a "region of interest" containing all relevant image information is defined. Only the image information in that region of interest is digitized and/or subsequently processed.

The captured, digitized image information of the region of interest is then compared to a threshold value in order to convert it to a binary form. Pixels having grey scale values above a predetermined threshold value are assigned one of two values (e.g., binary 1) to indicate that they are relatively "white," while pixels having grey scale values below the threshold value are assigned the other of the two values (e.g., binary 0) to indicate that they are relatively "black".

The binarized image data is then examined to identify all pixels which are at edges (i.e., transitions from black to white or vice versa) in the image. Edge pixels which are adjacent to one another are then associated with one another to define "blobs" in the image. The color of each blob (or "type") (i.e., whether it is black or white) is then determined, preferably by sampling one or more pixels within the blob. Parameters such as the sizes and colors of the various blobs are then analyzed to determine whether or not the substantially circular object has an acceptable appearance. For example, assuming that the substantially circular object is white against a black background, and further assuming that the substantially circular object is the largest component of the image, then the image should contain one relatively large white blob. Moreover, the perimeter of this relatively large white blob should be a certain size. If it is too small, the substantially circular object may be rejected as too small. If it is too large, the substantially circular object may be rejected as being too large, as having a flag, or as not having the desired substantially circular shape. Defects such as black eyes and by-passes are indicated when black blobs are detected within the above-mentioned large white blob. If a black blob of at least a predetermined minimum size is detected, the substantially circular object may also be rejected as having an unacceptable appearance.

The methods and apparatus of this invention preferably include separating substantially circular objects found to have an unacceptable appearance from those having an acceptable appearance. The invention also preferably includes providing the operator with current information regarding the number and/or rate of detected defects, and may also include a visual display of the objects being inspected, with special emphasis on those found to be defective.

Because by-passes and the background field of pixels are both processed as having a background color, and because of the close proximity of any by-pass to the background field, under certain conditions it may be difficult for a processor to distinguish a field of pixels depicting a by-pass from the field of pixels representing the background, because the two are separated by the relatively thin edge of the plug wrap of the cigarette filter. In many applications, the processor may not have sufficient resolution to detect the edge of the plug wrap. Accordingly, the pixel field representing the by-pass region may be processed as part of the background, which event will skew the inspection results. In such event, a cigarette having a by-pass defect may pass undetected.

This problem may also arise with respect to the detection of black-eyes or other stains which might occur along an edge of a cigarette filter.

Accordingly, further aspect of the present invention is the inclusion of a prismatic arrangement operative with the camera of the inspection apparatus so that imaging includes not only the end face of the cigarette filter but also peripheral regions along the sides of the cigarette immediately adjacent the end face. This arrangement and an adjustment of threshold values in the processor will assure that by-pass regions are spaced apart from the background field of the pixels so that by-pass defects (and any other defect located along the edge of the end face) are more consistently defined and detected.

BRIEF DESCRIPTION OF THE DRAWING

Details and further aspects of the present invention, its nature and various advantages will become more apparent from the following detailed description of the preferred embodiments with reference to the drawing, in which:

FIG. 3 is a simplified elevational view of a portion of illustrative cigarette making machinery showing how the appearance inspection apparatus of this invention can be added;

FIG. 4 is a schematic block diagram of illustrative appearance inspection apparatus constructed in accordance with a preferred embodiment of the present invention;

FIG. 15 is a side view of a truncated conical prism for use in an apparatus as shown in FIG. 13;

FIG. 16 is side view of a hemispherical prism for use in an inspection apparatus as shown in FIG. 13;

FIG. 17 is a perspective view of a pyramid shaped prism for use in an inspection apparatus as shown in FIG. 13;

FIG. 18 is a depiction of typical image data of the type produced by an inspection apparatus of the type shown in FIG. 13, but having instead a prism as shown in FIG. 17;

FIG. 19 is a perspective view of an end of a cigarette showing regions imaged by an inspection apparatus of the type shown in FIG. 13, but having instead a prism of the type shown in FIG. 17;

FIG. 20 is a perspective view of a rectangular prism for use in an inspection apparatus of the type shown in FIG. 13; and FIG. 21 is a depiction of typical image data produced by an inspection apparatus of the type shown in FIG. 13, but having instead a prism as shown in FIG. 20.

DETAILED DESCRIPTION OF THE PREFERRED EMBODIMENTS

Figure 1:
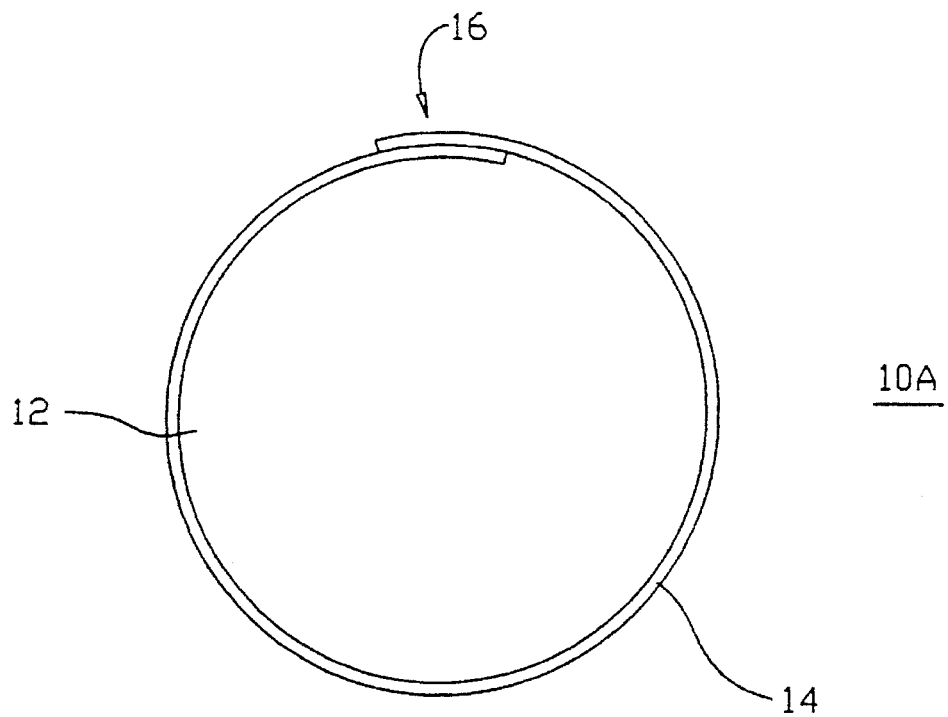
FIG. 1 is a simplified end view of the filter on a filter tipped cigarette, the appearance of which is to be inspected in accordance with the principles of the present invention.

Referring to FIG. 1, a typical substantially circular object 10A to be inspected in accordance with the present invention is exemplified as the filter end of a filter-tipped cigarette. It is to be understood that the invention is equally applicable to inspecting the appearance of other substantially circular objects. For example, object 10A could be an end portion of a cigarette filter plug prior to its attachment to a tobacco rod or some other cigarette component.

The object 10A has an acceptable appearance in the illustrative application of the invention described herein. In particular, object 10A has a large, white, central region comprising one end of a bundle of cellulose acetate fibers as is commonly found in the construction of cigarette filters. This bundle of fibers is surrounded by one or more layers of paper 14. The layers of paper 14 hold the bundle of fibers together, give the bundle a smooth outer surface and hold the filter to the tobacco rod of the cigarette. Although more than one layer of paper might be present, only one representative paper layer 14 is shown in the object 10A of FIG. 1. The paper layer 14 is typically wrapped or formed around the underlying structure so that edge portions of the paper layer 14 overlap one another and are glued to form a side seam 16. Although the boundary between the fiber bundle 12 and the paper layer 14 is clearly depicted in FIG. 1, that boundary may not be as clearly visible in an actual product. The same is true of the overlapping paper layers along the seam 16.

Figure 2:
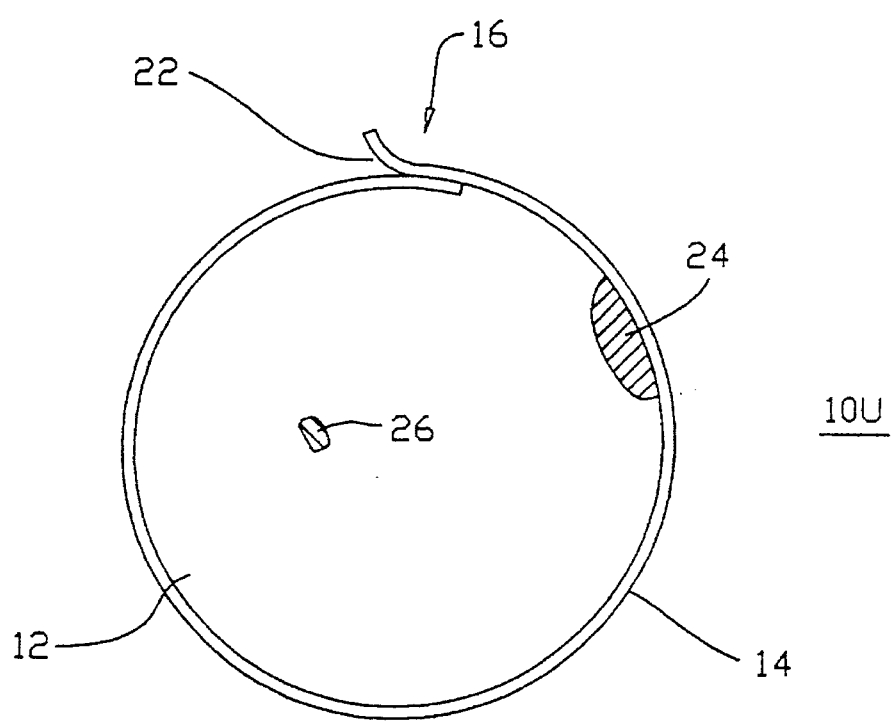
FIG. 2 is a view similar to FIG. 1 showing the end of a cigarette filter having several representative defects in appearance.

Referring to FIG. 2, a substantially circular object 10U is generally similar to the object 10A, but includes several representative defects in appearance, any one of which may render the appearance of the object 10U unacceptable. One of the defects in the object 10U is that the side seam 16 is not completely glued down, leaving a so-called "flag" 22 of paper extending out from one side of the cigarette filter. Such flags 22 may be caused by a number of malfunctions in the cigarette making process such as an under-sized or over-sized fiber bundle 12, an insufficient application of glue along the seam 16 or a snag in the machinery which lifts and/or curls a portion of the paper 14 at the seam 16. Whatever the cause, the flag 22 renders the product unacceptable to the consumer, and it is important to promptly reject all cigarettes having this defect and promptly undertake corrective action. Flags 22 comprise one type of defect which the present invention detects.

Another defect which may affect the appearance of the object 10U is a gap 24 between the fiber bundle 12 and the paper 14. Such a gap is called a "by-pass" because it may allow some smoke to pass around the fiber bundle 12 without it being fully filtered. By-passes may be caused by a fiber bundle which is improperly shaped or too small, a paper layer 14 which has not been fully pressed against the underlying fiber bundle, or some other similar problem arising at the cigarette maker or the filterplug maker. A by-pass 24 will tend to show up as a relatively dark region, especially when the objects 10U are illuminated obliquely in accordance with the present invention as described in detail below.

Still another type of defect in the appearance of the object 10U is a discolored region 26 on the face of the fiber bundle 12. The discolored region 26 may have several causes, such as an accidental staining of a portion of fiber bundle 12. With charcoal filters, such as those comprising a charge of charcoal particles retained between two axially spaced plugs of cellulose acetate, a discolored region 26 may appear at the filter end face if a bit of charcoal escapes from within the filter structure. The latter type of discolored region is known as a "black eye," but for convenience herein, all discolored regions on the fiber bundle 12 will be referred to as black eyes.

The inspection apparatus 40 of the present invention can be operated at any convenient location in an apparatus which produces or otherwise handles substantially circular objects to be inspected. Referring to FIG. 3, a preferred location for the image-capturing portion 42 of the inspection apparatus 40 is in a conventional filter tipped cigarette manufacturing equipment (see also FIG. 4), such as a conventional Max model tipper available from Hauni-Werke Korber & Co. KG of Hamburg, Germany. In such tipping machines, fully finished filter-tipped cigarettes having end faces 10 are conveyed one after another at spaced locations along the cylindrical surface of a conventional Hauni inspection drum 30. As the drum 30 rotates, the Hauni apparatus performs certain conventional inspection operations on the cigarettes located along that drum. The cigarettes are then transferred to a conventional Hauni rejection drum 32. The Hauni apparatus rejects defective cigarettes by pneumatically removing the defective cigarettes from the drum 32. Acceptable cigarettes are allowed to continue and are transferred to an exit drum 34, which conveys the cigarettes out of the tipping machine (by transferring them to a conventional tray filler or a mass flow conveyor system (not shown)).

It is convenient to locate the image-capturing portion 42 of the apparatus of the present invention adjacent a relatively upstream portion of the rejection drum 32. The reject output signals of the present apparatus can either be used as an additional input to the conventional Hauni reject mechanism or be used in cooperation with a separate reject mechanism 44 that is added to the rejection drum 32 at a downstream location.

Referring to FIG. 4, the inspection apparatus 40 includes an arrangement which differentiates (contrasts) the objects 10 from their background. Preferably the inspection apparatus 40 cantilevers the end faces 10 of the cigarettes away from the adjacent portion of the drum 32 as the cigarettes are conveyed past the camera 46. To further contrast the end surfaces 10 from their background, surfaces of the drum 32 adjacent the camera 46 is preferably dark and non-reflective, and the end surfaces 10 are obliquely illuminated by light from the light source 48. In particular, a fiber optic bundle 49 directs light from the light source 48 at an angle of incidence of approximately 45° relative to the end face 10 of the cigarette as each cigarette is brought directly opposite the camera 46 for imaging. The axis along which the camera 46 images the end face 10 of the cigarette is substantially perpendicular to the plane of the end face 10 of the cigarette.

Although the drum 32 rotates continuously, the light source 48 may briefly illuminate or "strobe" each time the end face 10 of a cigarette is positioned directly opposite the camera 46. This arrangement has the effect of effectively stopping or "freezing" the motion of the cigarette being imaged so that the camera 46 forms a still or nearly still image of the end face 10 of cigarette. The image-capturing and image-processing apparatus 40 of the present invention is synchronized with the motion of cigarettes and the drums 30, 32, and 34 by a shaft encoder 50 which produces an output signal pulse each time the drum apparatus has moved by a predetermined amount. This connection enables the processor 52 to resolve exactly when an end face 10 of a cigarette is located directly opposite camera 46. The processor 52 then strobes the light source 48 and begins the process of reading out or "grabbing" the cigarette image captured by the camera 46.

In order to save time in the image grabbing operation in applications in which the significant image information does not fill the entire field of view of camera 46, the camera is preferably positioned so that the significant image information is in the portion of the field of view which is scanned first when an image is grabbed from the camera. In addition, the scanning is stopped as soon as the portion of the field of view containing the significant image information has been scanned.

Figure 5:
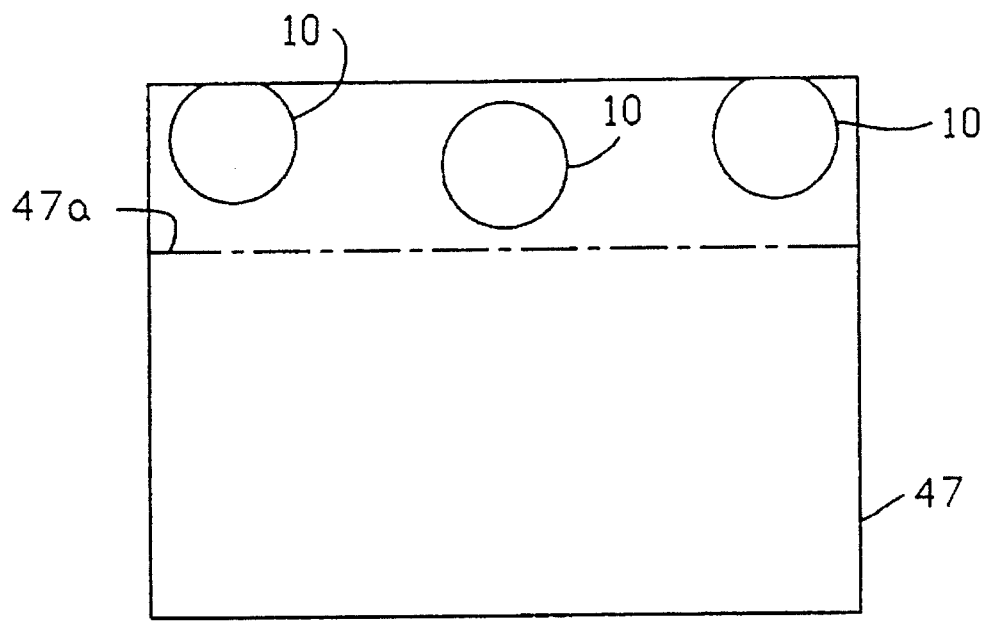
FIG. 5 is a simplified depiction of a typical image captured by the video camera in the apparatus of FIG. 4.

The above scanning principle is described with reference to FIG. 5, wherein the typical field of view 47 of the camera 46 is 640 pixels wide by 480 pixels high. The camera 46 is typically scanned horizontally from top to bottom. Accordingly, the camera 46 is placed relative to the objects to be imaged so that the significant image information is at the top of the field of view of the camera. In particular, in imaging the end faces 10 of the cigarettes, an image of an appropriate size is contained within an area less than about 150 by 150 pixels in the field of view 47. The processor 52 is programmed to scan camera 46 down only until 150 vertical pixels have been scanned, i.e., the scanning operation stops when the line 47a is reached. Although only the central cigarette image 10 in FIG. 5 is of interest, the field of view 47 may include portions of adjacent cigarettes on the drum 32. It will be explained below how this extraneous image information is also eliminated from consideration. By scanning only a limited portion of the field of view each time an image is to be captured, the rate at which the apparatus can capture and process images is substantially increased.

Figure 6A:
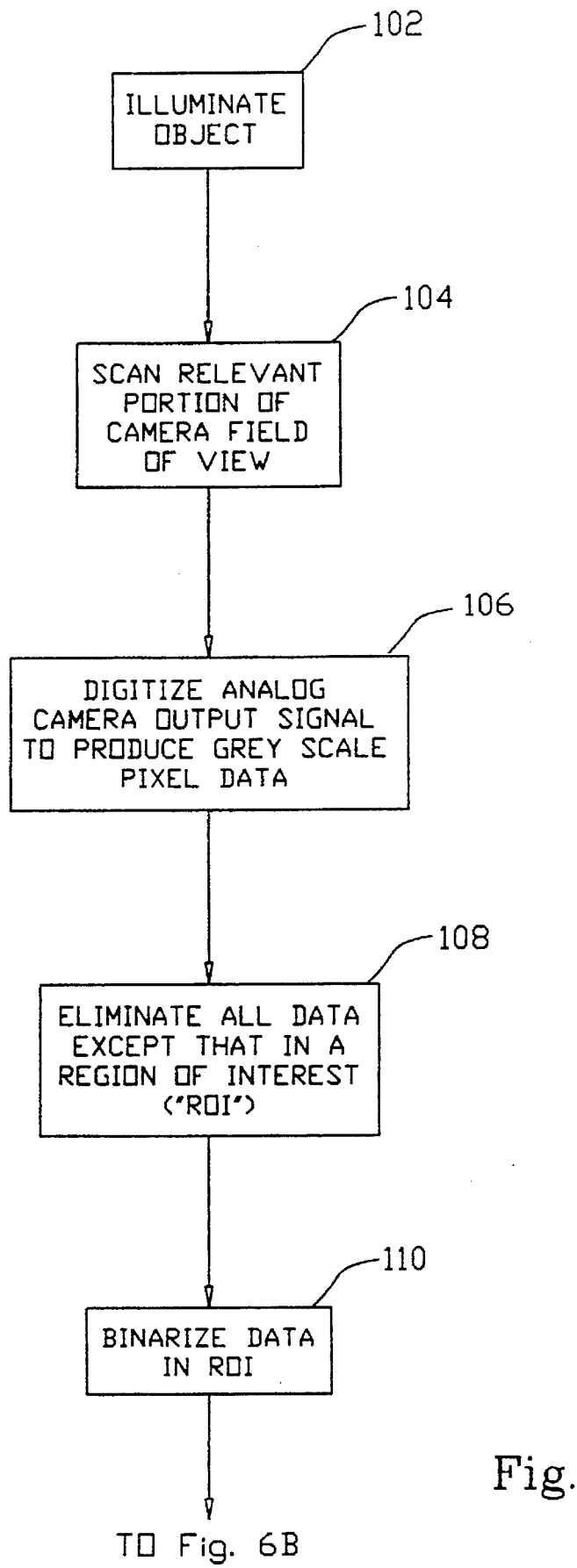
FIGS. 6a and 6b (referred to collectively as FIG. 6) are flow charts of steps in the preferred method of appearance inspection, which steps are executed by the apparatus of FIG. 4 in accordance with a preferred embodiment of the present invention.
Figure 6B:
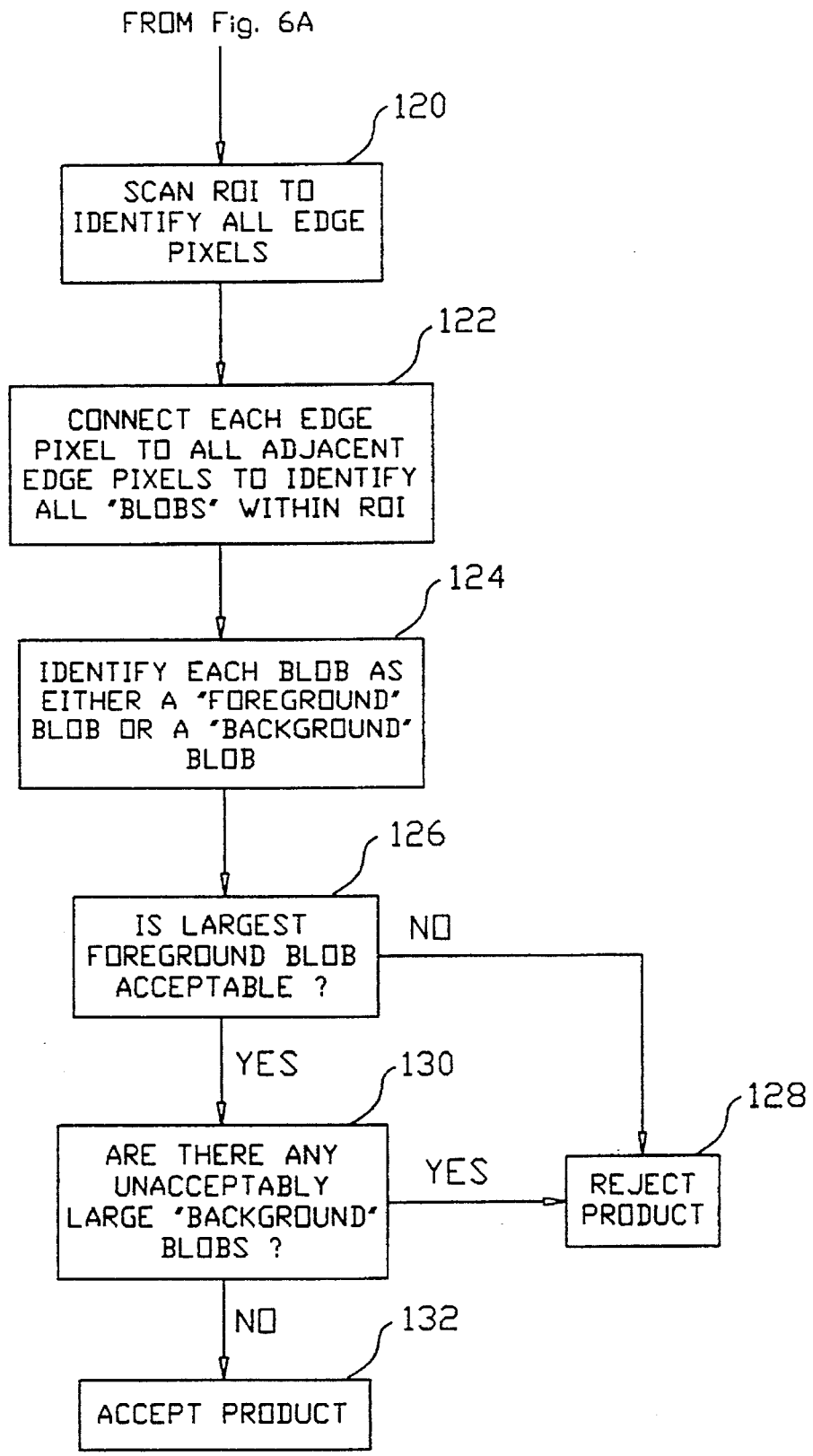

FIG. 6 sets forth steps which may be performed by the apparatus 40 in order to perform an appearance inspection operation in accordance with the preferred embodiment of the present invention. Most of these steps are executed or at least controlled by the processor 52 which preferably comprises a programmable, general purpose digital computer such as a conventional Intel Model 386 or 486 microprocessor or a compatible backplane into which a conventional frame grabber and image grabber boards (such as those available from Pattern Processing Technologies, Inc. of Eden Prairie, Minn.) can be plugged.

In step 102, the processor 52 causes the light source 48 to briefly illuminate the end face 10 of a cigarette as the cigarette arrives at a location directly opposite the camera 46. As described above, the processor 52 resolves when a cigarette is properly positioned opposite the camera 46 from a signal that it receives from the shaft encoder 50. The processor begins an inspection cycle by illuminating the end face 10 of the cigarette.

In step 104, the processor 52 scans the relevant portion of the field of view of the camera 46 (e.g., as described above in connection with FIG. 5). Thus, for example, the processor 52 may only scan the portion of the field of view 47 of the camera 46 down to the line 47a. The output signal of camera 46 is typically an analog signal.

In step 106, the processor 52 digitizes the analog output signal from the camera 46 to produce digital grey scale pixel data representative of the analog output signal. In this digital data, each pixel is represented by a digital value (e.g., from 0 to 255) indicative of the level of brightness of the corresponding portion of the image received by camera 46. Assuming that the field of view of the camera 46 is 640 pixels wide, and that line 47a is 150 pixels below the top of the camera screen, the grey scale image data will cover an area 640 pixels wide by 150 pixels high.

Figure 7:
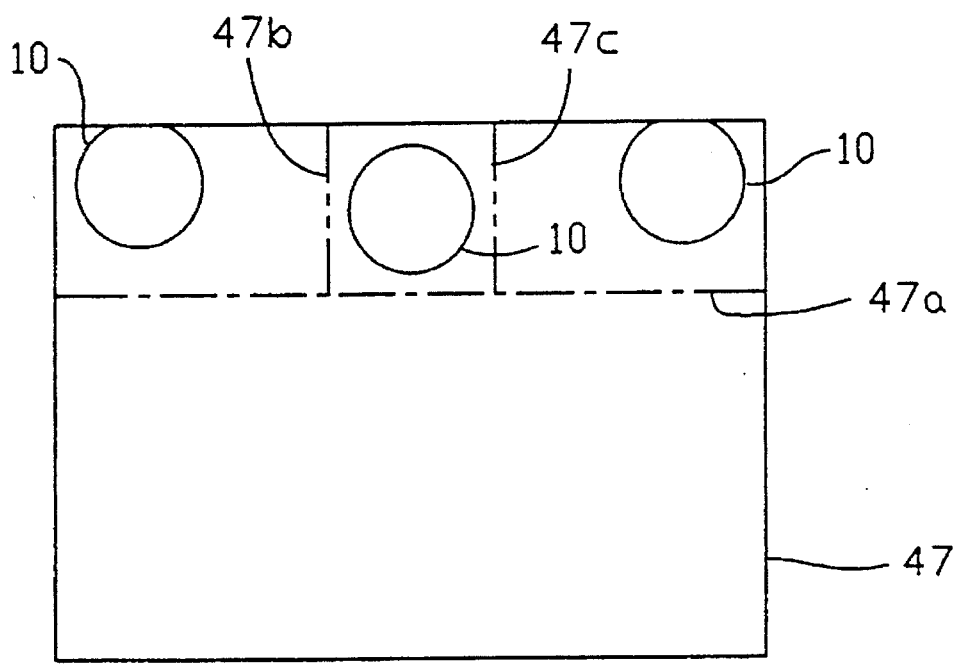
FIG. 7 is a view similar to FIG. 5 showing how the image may be restricted to a particular region of interest in accordance with a preferred embodiment of the present invention.

Assuming that the significant image information is contained in only a portion of the above-mentioned area, the processor 52 performs a step 108 to limit further processing of the image data to just that portion of the image area containing significant information. In the illustrative embodiment being described, the significant image information is within the 150 pixels in the horizontal center of the field of view of the camera 46. Accordingly, and in reference to FIG. 7, in step 108, the processor 52 limits all further consideration of the digital image data to the data between the vertical line 47b (245 pixels to the right of the left-hand edge of the field of view 47) and the vertical line 47c (245 pixels to the left of the right-hand edge of field of view 47). The area bounded by the top of field of view 47 and by the lines 47a–c is referred to in subsequent steps as the "region of interest" or "ROI".

In step 110, the digital grey scale image data for each pixel in the ROI is compared to a threshold value which is selected to achieve separation between relatively light pixels and relatively dark pixels. For example, this threshold value is preferably chosen so that all pixels associated with the background around the white or relatively light cigarette end face 10 in the ROI will have values on one side of the threshold value, while all pixels comprising the image of cigarette end 10 (assuming that it is of acceptable appearance) will have values on the other side of this threshold value. Assuming, for example, that relatively light pixels have values above the threshold value, those pixels are assigned one of two "binary" values (e.g., 1) for further processing. All other pixels are assigned the other of the two "binary" values (e.g., 0).

Although the traditional binary values 0 and 1 are used in the description above, it is to be understood that any other sets of values (e.g., −1 and 1) can be used instead, and all such alternatives are embraced by the term binary as used herein to respectively identify pixels having grey scale values above or below the threshold value used to differentiate "light" pixels from "dark" pixels. It will be appreciated that the techniques mentioned above (e.g., the oblique lighting from fiber optic bundle 49, the cantilevering of the cigarette ends from drum 32, and the darkening of adjacent surfaces of the drum 32 opposite camera 46) all help to ensure that the processor 52 (in step 110) readily separates the relatively light cigarette end face 10 from the relatively dark surrounding background field.

Figure 8:
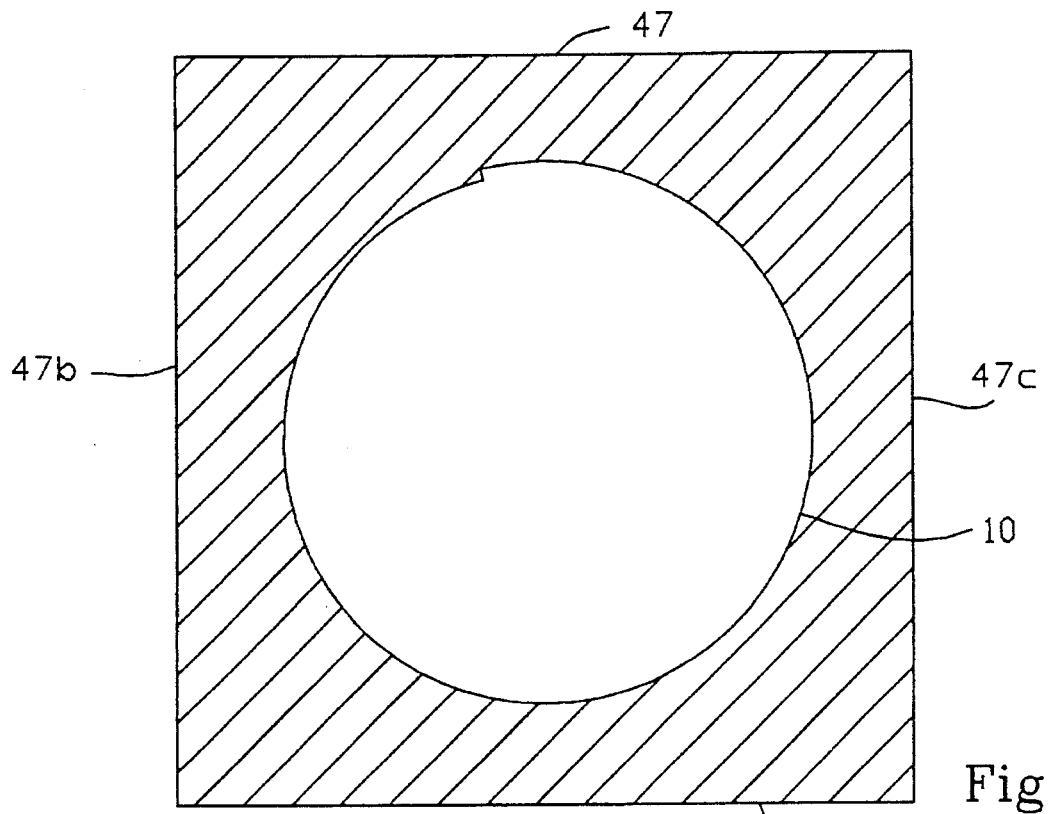
FIG. 8 is a simplified depiction of typical image data during processing in accordance with the method steps of FIG. 6.

FIG. 8 shows how the image of an end face 10 of an acceptable cigarette may appear in the ROI after the execution of the step 110. In FIG. 8, the dark background pixel region is shaded, while the light "foreground" pixel region is unshaded.

In step 120, the processor 52 scans the ROI to identify all "edge" pixels (i.e., pixels which are at transitions between light and dark image regions). This step 120 is preferably performed by starting with the top row of pixels and scanning the rows one after another from left to right. With the example shown in FIG. 8, each scanned row will start with dark pixels. After the first few all-dark rows, the scanning operation of step 120 will encounter rows which initiate with a first series of dark pixels followed by a series of light pixels. The first light pixel at the transition between dark and light pixels is identified as an edge pixel. Scanning will then continue through successive white pixels until the next encountered pixel is another dark pixel. The immediately preceding light pixel is then identified as another edge pixel. This scanning process continues until the entire ROI has been scanned and all edge pixels have been identified.

Figure 9:
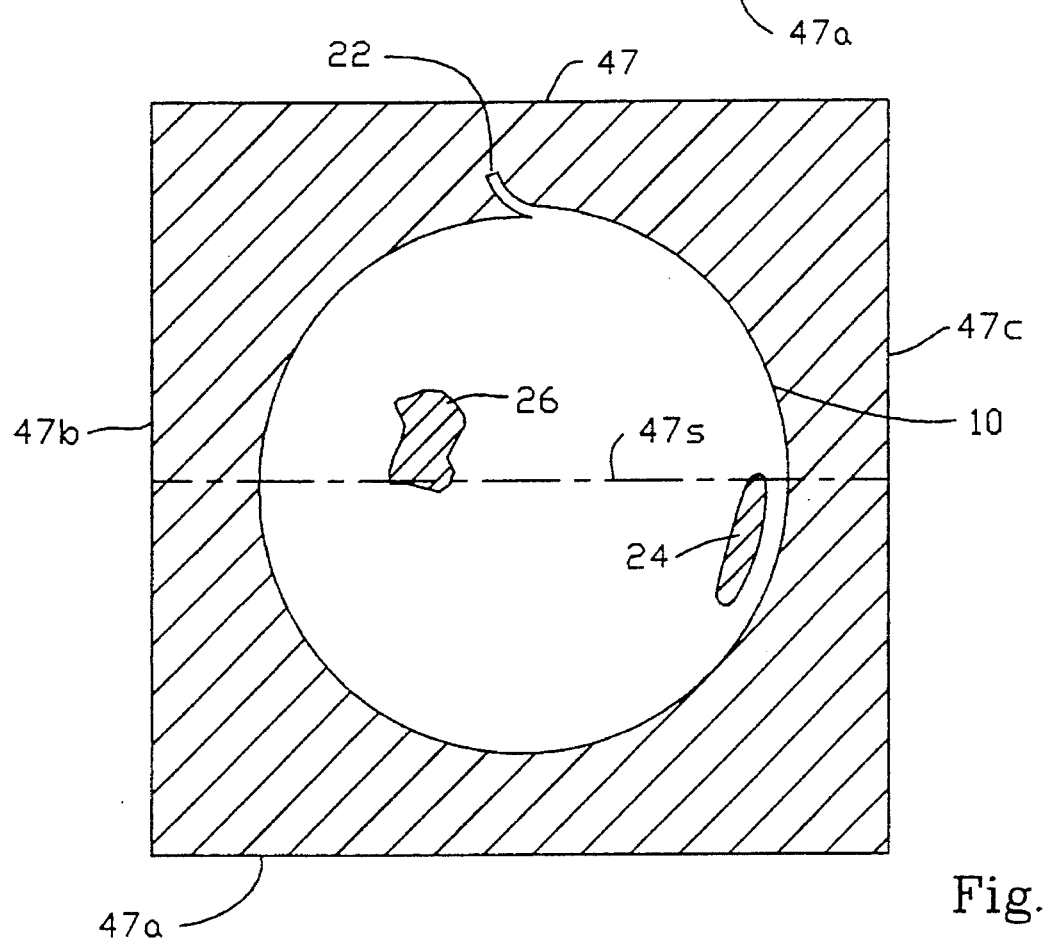
FIG. 9 is similar to FIG. 8 and shows other typical image data;.

FIG. 9 is similar to FIG. 8 but shows an end face 10 of an unacceptable cigarette having several defects of the type described above in reference to FIG. 2. The threshold level discussed above in connection with the step 110 is preferably chosen to make defects such as the by-pass 24 and the black eye 26 appear as dark regions like the background region surrounding the image of the end of the cigarette. It is to be appreciated that when the image of FIG. 9 is scanned for edge pixels in step 120, many more edge pixels will be encountered than are encountered in scanning the acceptable cigarette image shown in FIG. 8. For example, with the unacceptable cigarette, there will be extra edge pixels associated with the flag 22, the by-pass 24 and the black eye 26.

In scanning from left to right along the line 47s in FIG. 9, the scanning operation will first encounter several dark pixels and then a first light pixel associated with the perimeter of cigarette end face 10. This first light pixel is identified as an edge pixel. After that, several light pixels are encountered until the edge of black eye 26 is reached, at which point the last light pixel is identified as an edge pixel. The black eye 26 is traversed as a succession of dark pixels until a first light pixel to the right of the black eye 26 is encountered. This latter light pixel is identified as yet another edge pixel. More light pixels follow until the left-hand edge of the by-pass 24 is encountered, at which point the last light pixel is identified as another edge pixel. The by-pass 24 is then traversed as a succession of dark pixels until the first light pixel associated with the wrapper around the cellulose acetate fiber bundle is encountered. This first light pixel is identified as yet another edge pixel, and the last light pixel just before the right-hand dark background region is identified as still another edge pixel. Accordingly, instead of identifying only two edge pixels as would be the case in scanning along the line 47s in the acceptable of FIG. 8, six edge pixels are identified in scanning along the line 47s in FIG. 9.

Figure 10:
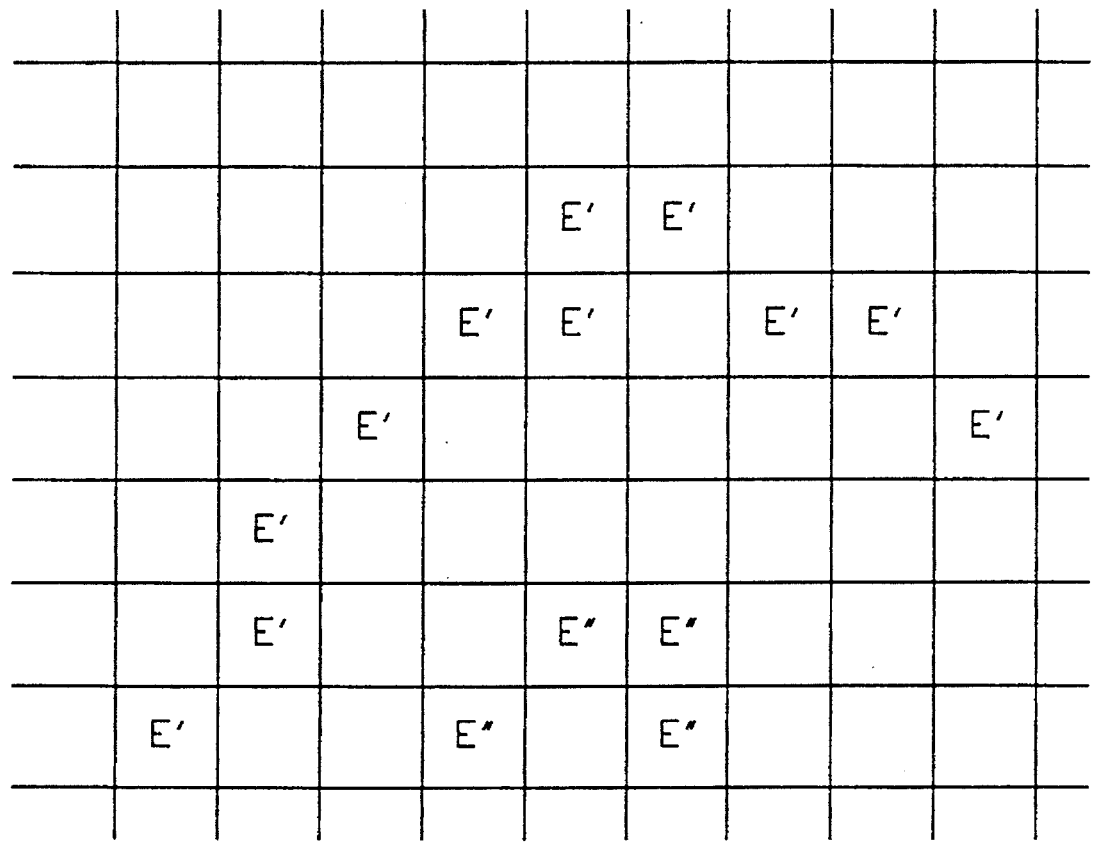
FIG. 10 is a simplified depiction of a typical region of pixels in image data of the type shown in FIGS. 8 and 9, with certain pixels identified by reference characters as having certain attributes.

In step 122, each edge pixel is connected to as many adjacent edge pixels as possible. In FIG. 10, each square represents one pixel, and all edge pixels are identified by the letter E. All E' edge pixels are considered to be adjacent to one another and are identified as one associated group of adjacent edge pixels. Similarly, all E" edge pixels are considered to be adjacent to one another and are identified as another associated group of adjacent edge pixels. Assuming that the significant image information is always completely surrounded by a dark background region, all groups of edge pixels identified in the step 122 will be closed shapes. Each of these closed shapes is referred to as a "blob." In FIG. 8, for example, there is only one large light blob. All edge pixels identified in connection with the image of FIG. 8 are associated with the periphery of that one large light blob. In FIG. 9, on the other hand, there is one large light blob containing two smaller dark blobs 24 and 26. Computer programs for performing this and subsequent blob identification and analysis is available from Pattern Processing Technologies, Inc. (mentioned above), and is part of PPT's 400 VPC Vision Program Manager Software.

In step 124, each blob that was identified in step 122 is examined as to its type, whether it is a light "foreground" blob or a dark "background" blob. This step is preferably performed, for example, by determining whether a single pixel inside the blob which is not also part of another blob is light or dark. If the pixel tested is light, then the blob is a light "foreground" blob. If the pixel tested is dark, then the blob is a dark "background" blob.

In step 126, the foreground blob having the largest number of associated edge pixels is tested for acceptability. For example, it may be known that the large light foreground blob in FIG. 8 should have a total of 480 to 530 edge pixels. If there is no foreground blob with this number of edge pixels, the image should be rejected (in step 128) as having an unacceptable appearance. If cellulose acetate fiber bundle 12 is significantly under-sized or over-sized, the largest foreground blob will have fewer than 480 or more than 530 edge pixels. Similarly, a flag 22 (FIG. 9) will increase the number of edge pixels of the largest foreground blob beyond the acceptable upper limit. If the cigarette is crushed or the like, that defect will also manifest a change in the total number of edge pixels of the largest foreground blob beyond the acceptable limits. Thus, comparing the number of edge pixels associated with the largest foreground blob enables the apparatus 40 to identify any of several possible defects in the image. If in the execution of the step 126, the largest foreground blob is not found to have a number of edge pixels within a predetermined acceptable range, then control passes to step 128 so that the associated product 10 can be rejected when it reaches the rejection mechanism 44 (FIGS. 3 and 4). On the other hand, if the image passes testing at the step 126, then control passes to step 130 where the image is further tested for acceptability.

In the step 130, the image data is tested for any unacceptably large background blobs. For example, it may be predetermined that any background blob having more than a certain number of edge pixels (e.g., nine or more) renders the associated image unacceptable. Accordingly, in the step 130, the number of edge pixels associated with each background blob is compared to this predetermined limit, and if any background blob is found to have more than the threshold number of edge pixels, control passes to step 128 to cause the associated product to be rejected. On the other hand, if the image has no excessively large background blobs, control passes to step 132 to allow the associated product to be accepted.

As has been mentioned, it can be important or at least helpful to provide the operator of the system with current information as to the results of the appearance inspection operation. Such provision may be done, for example, via a computer display screen 54 of the apparatus 40 (see again FIG. 4).

Figure 11:
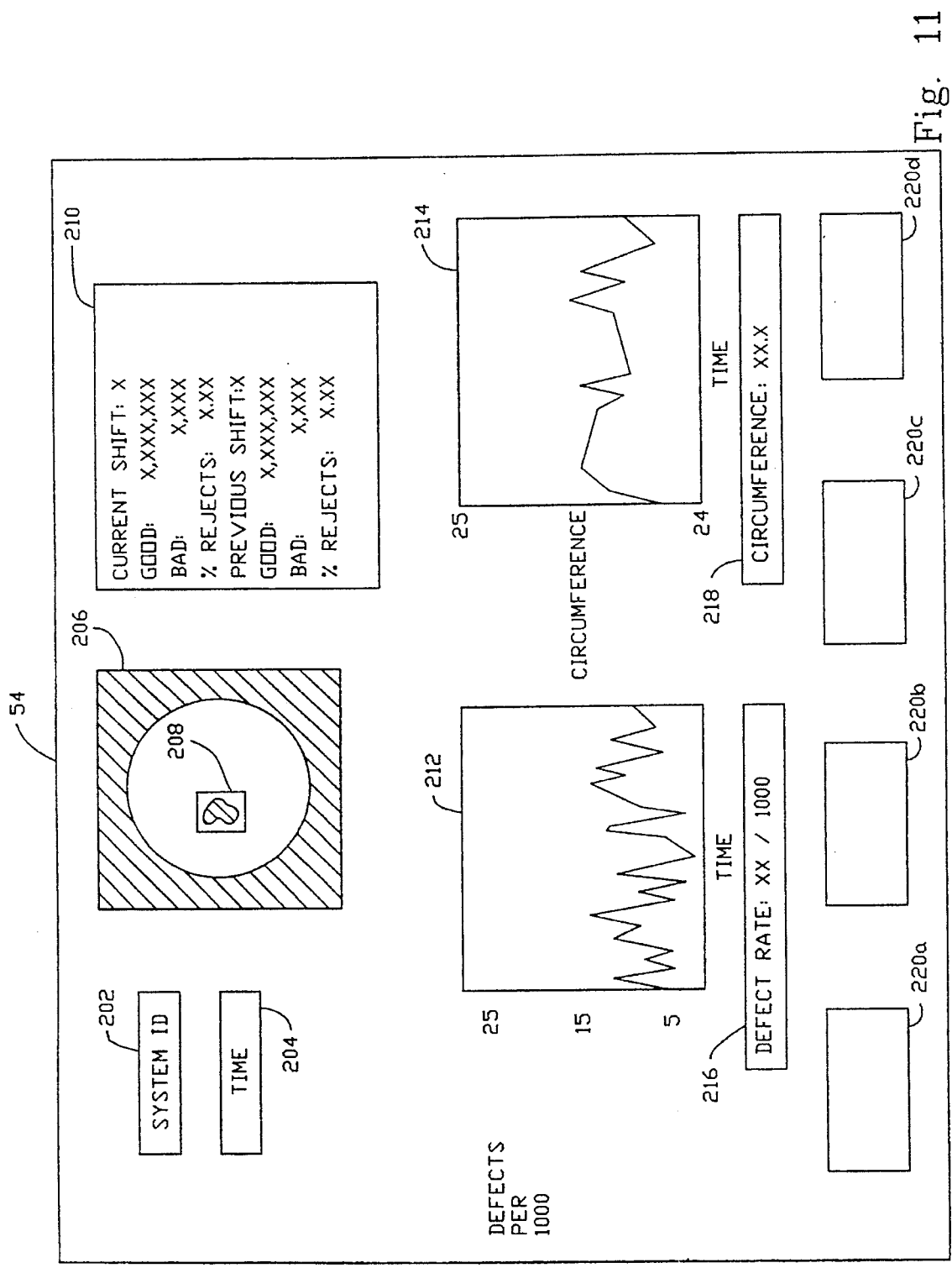
FIG. 11 is a simplified view of a preferred information display on a computer display panel viewable by the operator of an inspection system constructed in accordance with a preferred embodiment of the present invention.

Referring to FIG. 11, the preferred display on the screen 54 is controlled by the processor 52 and includes information fields as follows:

1. Field 202: an identification of the cigarette maker at which the inspection system 40 is operating;
2. Field 204: the time of day;
3. Field 206: the current digital grey scale image of the region of interest in the field of view of the camera 46. Preferably, when an image is identified as defective, that image is held longer than normal (e.g., for three seconds) to give the operator of the system more time to examine it. In addition, a rectangular box 208 is displayed around the defective portion of the image which caused the rejection;
4. Field 210: a table of cumulative data for the current shift of operation of the inspection apparatus 40, and similar data for the preceding shift of operation. For each shift, the data preferably includes (a) a shift identifier, (b) the number of acceptable cigarettes produced, (c) the number of defective cigarettes detected and rejected, and (d) the percent of total production rejected;
5. Field 212: a moving graphical representation or histogram showing recent experience of the system in terms of the number of rejects per 1000 cigarettes produced;
6. Field 214: a moving graphical representation or histogram showing recent experience of the system in terms of measured cigarette circumference;
7. Field 216: the most recent experience of the system in terms of the number of rejects per 1000 cigarettes produced;

8. Field 218: the most recent experience of the system in terms of measured cigarette circumference; and 9. Fields 220a–d: several "buttons" (assuming that the display 54 is a "touch screen") for the operator to control various functions of the inspection system. For example, one or more of buttons 220 can be used to tell the system about a shift change. Another button 220 can be used to reset the counters in the processor 52 which are used to accumulate the data shown in the field 210 for the current shift.

Figure 12:
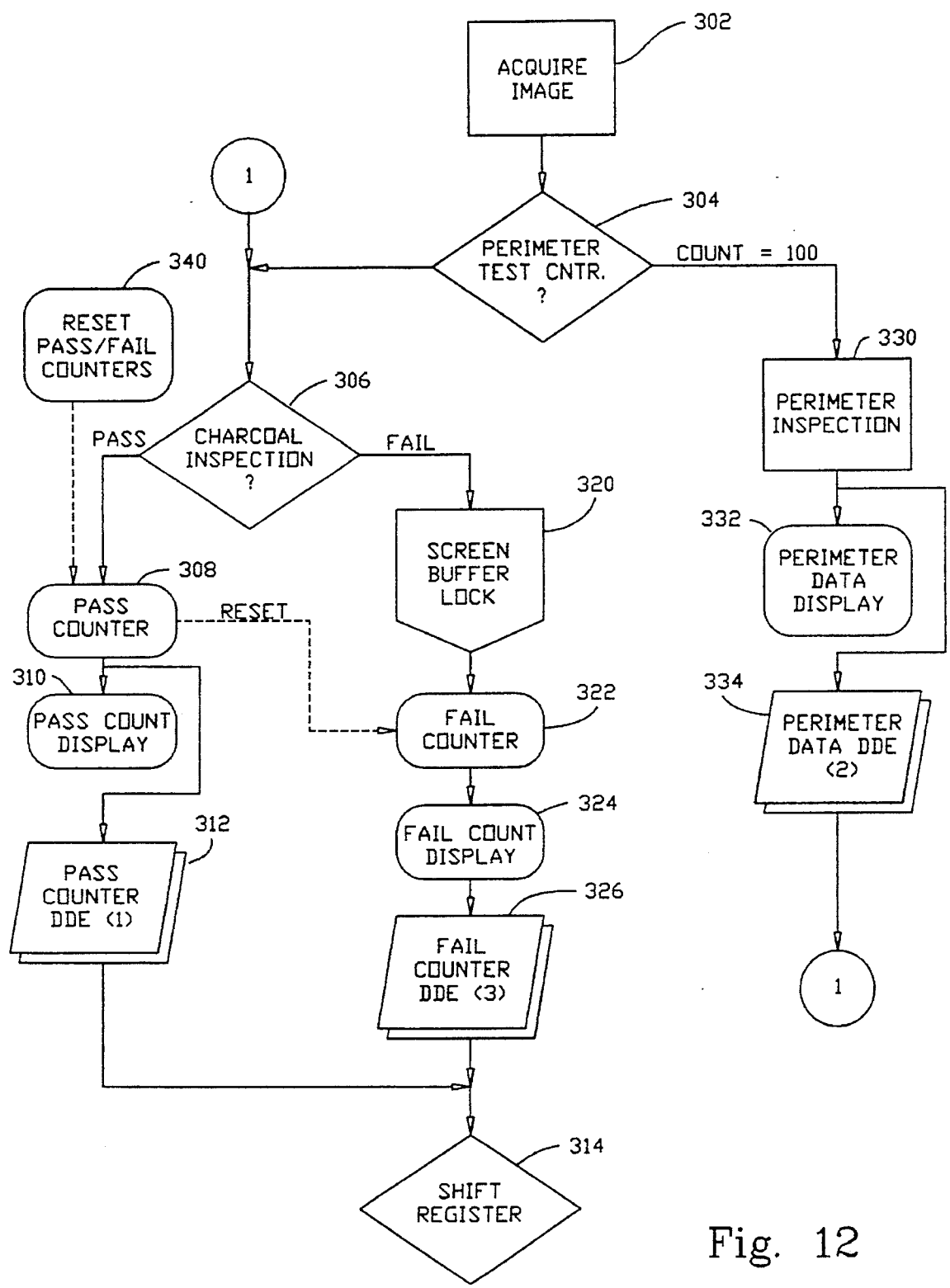
FIG. 12 is a flow chart of an alternative and/or additional appearance inspection steps which may be carried out by the apparatus of FIG. 4 in accordance with a preferred embodiment of the present invention.

FIG. 12 is a flow chart of operations which is preformed by the processor 52 to inspect cigarettes as described above and to support the display 54 as shown in FIG. 11. In step 302, the system acquires the next image to be inspected. This step can be performed as explained in more detail in the steps 102 through 124 in FIG. 6. If it is desired not to measure the perimeter or circumference of every cigarette, then in step 304 a perimeter test counter is to be incremented. The steps to the right of step 304 are then performed only each time the perimeter test counter reaches a predetermined number (e.g., 100). The steps to the left of step 304 are performed preferably for every cigarette.

In step 306, a so-called "charcoal inspection" is performed, which tests for the presence of unacceptably large background blobs as described in the step 130 of FIG. 6. Although the step 306 is referred to as "charcoal inspection" in FIG. 12, any sufficiently large black eye or by-pass will cause the associated image to fail this inspection step.

If the image passes the inspection step 306, control passes to step 308 in which a pass counter in the processor 52 is incremented.

In step 310, the associated portion of the field 210 on the display 54 is updated to reflect the new data in the pass counter.

In step 312 the new pass counter data is passed via an associated, conventional, dynamic data exchange ("DDE") to conventional computer programs which produce the histogram in the field 212 on the display 54. These computer programs may also produce the data shown in the field 216.

In step 314, appropriate data indicating that the cigarette just inspected has passed inspection is entered into a shift register in the processor 52. The shift register associated with step the 314 (sometimes referred to as the shift register 314) is shifted at the same rate that images are acquired in step 302. Data is entered into an upstream stage of the shift register. A downstream stage of the shift register is used as an output signal to control the reject mechanism 44 (FIGS. 3 and 4). The number of shift register stages between the upstream stage and the downstream stage corresponds to the time required for a cigarette to travel from the location at which its image is acquired in step 302 to the location at which it is rejected, if necessary, by the reject mechanism 44. When the step 314 is reached from the step 312, the data entered into the shift register will cause the reject mechanism 44 to allow the acceptable cigarette to pass unrejected.

If the cigarette fails the inspection test of the step 306, then control passes from the step 306 to a step 320. In the step 320, the processor locks the image displayed in the field 206 for a predetermined time interval (e.g. three seconds), and also augments that image with an appropriate rectangle 208 around the background blob which caused the image to fail the test 306.

In test 322, a fail counter in the processor 52 is incremented, and in step 324, the new fail counter data is used to update the appropriate portion of the field 210 on the display 54.

Step 326 is similar to above-described step 312 and involves passing the new fail counter data to the above-mentioned computer programs which produce the histogram in the field 212 and the data in the field 216 on the display 54.

When the step 314 is performed after performance of the step 326, the data entered in the shift register 314 will cause the defective cigarette to be rejected when that cigarette reaches the reject mechanism 44.

Although the perimeter inspection of step 330 could be performed for every cigarette (as described for the step 126 in FIG. 6), in the embodiment shown in FIG. 12 that inspection is only performed on every 100th cigarette. Accordingly, when a 100th cigarette is detected, perimeter inspection test 330 is performed on the image data as described above in connection with step 126. In particular, the number of edge pixels associated with the largest foreground blob in converted to a perimeter measurement by multiplying the number of edge pixels by a predetermined scale factor.

In step 332, the perimeter data in the field 218 on the display 54 is updated.

In step 334, the new perimeter data is passed to conventional computer programs which produce the histogram in the field 214 in a manner similar to the above-described steps 312 and 326. Control then passes from the step 334 to the step 306 so that charcoal inspection can be performed on the cigarette which has just been used to provide updated perimeter data.

Step 340 is performed whenever it is desired to reset the pass counter associated with the step 308 and the fail counter associated with the step 322. For example, the step 340 may be performed whenever there is a shift change.

Referring now to FIG. 9, one can appreciate that along the scan line 47s, certain boundary pixels of the by-pass region 24 are separated from background pixels by only the thickness of the paper layer 14. With some cameras and/or lighting conditions and/or operating speeds, the camera 46 may not be able to resolve the by-pass gap 24 from the background field. Accordingly, the processor 52 might in some circumstances process the by-pass gap 24 as part of the background field, letting the defect pass undetected. This problem can also arise when black eyes or other stains are located at or along the edge of the end face 10 of a cigarette.

Figure 14:
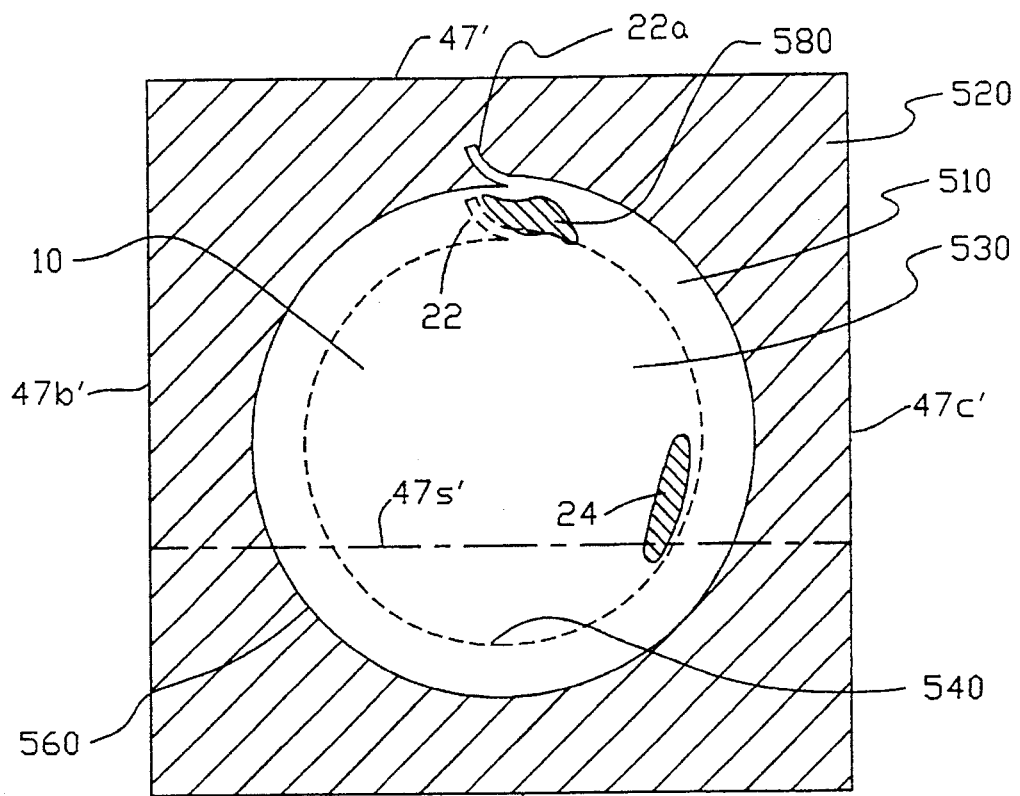
FIG. 14 is a depiction of a typical image data obtained during processing in accordance with the method steps of FIG. 6 as executed with an apparatus as shown in FIG. 13.
Figure 13:
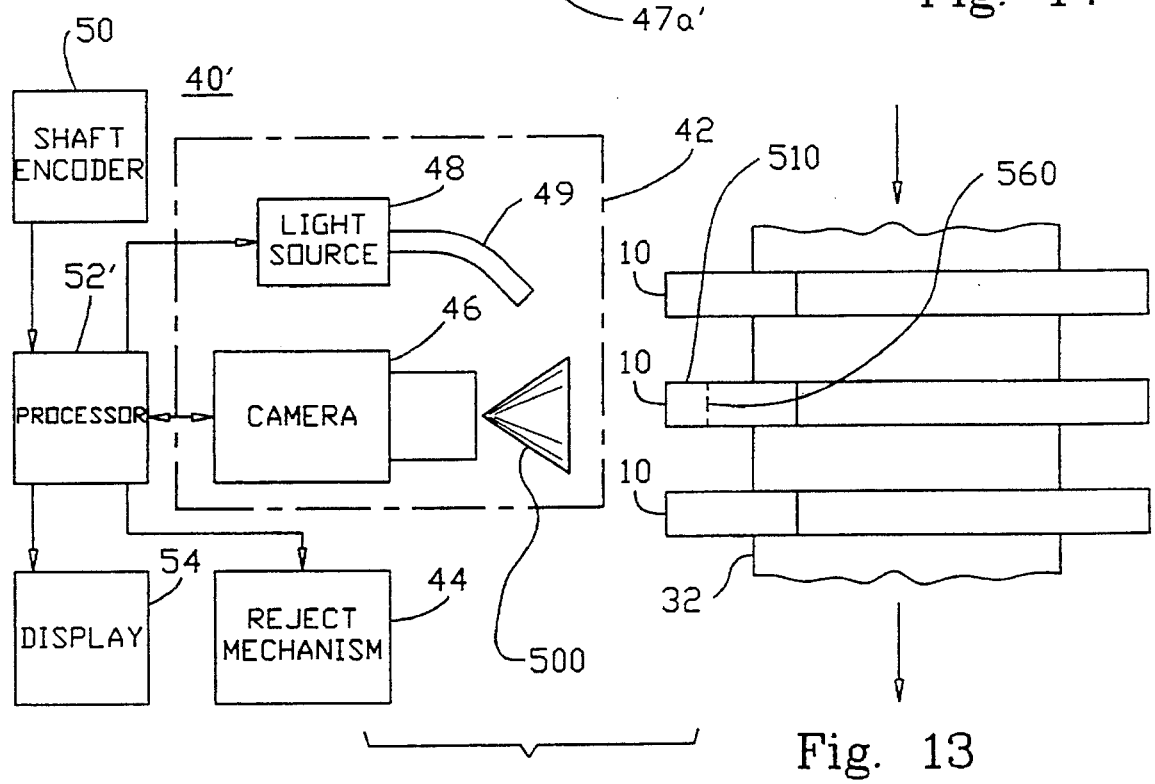
FIG. 13 is a schematic block diagram of an inspection apparatus constructed in accordance with another embodiment of the present invention.

Referring now to FIGS. 13 and 14, a preferred embodiment of the present invention includes a new image-capturing and image-processing apparatus 40' which has construction and functions similar to those of the apparatus 40 described above with reference to FIG. 4, but with the addition of a prismatic arrangement 500 as part of the image-capturing portion 42 of the appearance inspection apparatus 40'. The prismatic arrangement 500 is arranged and oriented relative to the camera 46 so that the image grabbing operation of the camera 46 includes both the end face 10 of a cigarette and a peripheral region 510 along the sides of the cigarette immediately adjacent the end face 10 of the cigarette. The prismatic arrangement 500 directs light scattered from the peripheral region 510 into the field of vision of the camera 46.

Preferably, the prismatic arrangement 500 comprises a conical prism aligned along the focal axis of the camera 46, with the apex of the prism 500 directed toward the camera 46. The conical prism 500 tends to produce a more linear imaging of the peripheral region 510 as one progresses from the proximal end face 10 of the cigarette 10 toward the distal end of the cigarette.

Referring now to FIG. 14, the processor 52' of the inspection apparatus 40' is arranged such that scanning stops when a line 47a' is reached and the field representing the region of interest (ROI) remains defined between the lines 47b' and 47c'.

As with the other embodiments, in a step 110, the processor 52' compares the digital gray scale image data for each pixel in the ROI to a threshold value which is selected to provide definition between relatively light pixels (foreground) and relatively dark (background) pixels. However, the selection of a threshold value is adjusted to accommodate the inclusion of the peripheral region 510 in the ROI. In particular, the ROI includes a field of pixels (image data) 520 relating to the background region, and a field of pixels representative of the end of the cigarette 10' as in the other embodiments, together with a third set of pixels representative of the peripheral region 510. Usually, the pixels associated with the background region 520 will have gray scale values close to the value of 25, whereas an unblemished cigarette end face 10 may produce a field of pixels 530 which are at or about the upper range of gray scale values nearer to 255 (the field of pixels 530 representative of the cigarette end face 10 is enclosed by the imaginary dashed line 540 in FIG. 14). However, the pixels corresponding to the peripheral region 510 (located outside the dashed line 540 in FIG. 14) may have gray scale values intermediate of those values associated with the background 520 or those of the end face pixels 530. If the tipping of the cigarette includes cork tipping paper, the pixels corresponding with the peripheral region 510 may have gray scale values as low as 50. In this embodiment, the threshold value against which the pixels of fields 510, 520 and 530 are to be compared is selected such that the end face field 530 and peripheral field 510 are differentiated from the background field of pixels 520. Accordingly, should the peripheral field of pixels 510 have a gray scale value as low as 50, the threshold value might be selected at 35 so that both the cigarette end face 10 and the peripheral region 510 are assigned the same binary value.

As a result, a border is no longer defined in the processed image along the periphery of the cigarette end face 10, which might have otherwise occurred along the imaginary dashed line 540.

Accordingly, as scanning progresses from left to right along the line 47s' in FIG. 14, the processor 52' will first detect a series of dark pixels associated with the background field 520. The processor will then detect light foreground pixels beginning at the distal edge 560 of the peripheral region 510. The processor 52' will continue to register light foreground pixels as the scanning continues along the line 47s' through region 510 and into region 530 until such time that the scanning operation reaches the edge pixel of the by-pass 24, whereupon the processor 52' will identify the last light pixel as an edge pixel. Further dark background pixels are encountered until the by-pass region 24 is traversed. As the first light pixels to the right of the by-pass 24 are encountered, another edge pixel is identified. Detection of further light foreground pixels continues as scanning progresses further to the right along the remainder of the fields 530 and 510.

As with the other embodiments, at processing step 122, the processor 52' associates each adjacent edge pixels to resolve closed shapes (blobs) and a determination is made in step 124 by the processor 52' to determine whether each blob is a light "foreground" blob or a dark "background" blob, preferably by resolving whether a single pixel inside a defined blob is either light or dark. In this embodiment, the largest blob will be defined along the distal edge 560 of the peripheral region 510 and not along an edge of the cigarette end face 10. Accordingly, the defined blob associated with the by-pass 24 is spaced away from the background pixel field 520 by the imposition of the light pixels which correspond with the peripheral region 510 of the cigarette. Accordingly, the processor 52' more readily distinguishes the by-pass region 24 from the background field of pixels 520. It is to be appreciated that in the other embodiments, the by-pass region 24 had been separated from the background pixels by pixels representative of the edge of the paper layer 14 at the end face 10.

It is to be appreciated that the processor 52' of the present embodiment can execute step 126 to resolve the number of associated edge pixels that comprise the largest light foreground blob to resolve whether the filter tipping is undersized or oversized or contains a flag 22a as described with reference to the other embodiments. The edge pixels however will be counted along the border describing the distal edge 560 of the cigarette tipping.

However in most circumstances, the angulated illumination provided from the light source 48 will cause a flag 22 to cast a shadow across a portion of the end face 10 and/or the peripheral region 510. The shadow will appear in the processed image as another discolored region 580, which the processor 52' will detect and define as a background blob of sufficient size to warrant rejection.

It is also possible that the dark blob 580 resulting from a flag 22 may extend entirely across the peripheral pixel field 510 to be considered by the processor 52' as part of the background field of pixels 520. In such case, the pixel count along the distal edge 560 would be increased to a value sufficient to indicate the presence of a defect. However, it is preferred to avoid this problem by configuring the prismatic arrangement 500 such that the peripheral region 510 (the peripheral region viewable by the camera 46) is extended sufficiently beyond any shadow that might be cast by a flag 22. Preferably, such arrangement places the distal edge 560 of the peripheral region 510 at a location approximately one-third to one-half of the length of the cigarette from the end face 10.

It is to be appreciated that the present invention may also be practiced as described with reference to FIG. 14 alternately with practice of the invention as described previously with reference to FIG. 9, so as to further facilitate the detection of flags 22. Such an arrangement would include analysis of the perimeter of the end face 10 (which corresponds with the imaginary line 540 in FIG. 14) for size and for the presence of flags as described in the previous embodiment together with execution of a second analysis for black eyes and by-passes at the end face 10 of the cigarette using the technique of the latter embodiment, wherein imaging is shifted to include the peripheral region 510 adjacent the end face 10 of the cigarette, wherein the peripheral region 510 is included as part of the light (foreground) pixel field. Such shifting in the image between operations may be effected by having the process or 52' switch the threshold value in the step 110 from one value which excludes the region 510 from the largest light (foreground) blob to a second value which includes it. In the alternative, the processor 52 may be configured to define two ROI's instead of one in the scanned field of FIG. 7, with the processor 52 executing one or the other of the two techniques on each of the two ROI's simultaneously or sequentially Referring now to FIG. 15, the prismatic arrangement 500 may employ prisms of different shapes, including a truncated conical section having a central prismatic portion 610 for imaging the cigarette end face 10 and outer prismatic portions 620 for capturing the image of the peripheral region 510 along the sides of the cigarette.

In the alternative, a semi-spherical prism might be used instead of a conical one as shown in FIG. 16.

Referring to FIG. 17, the prismatic arrangement 500 may comprise a prism in the form of a pyramid, whose corner portions 650 create radially extended regions of foreground pixels 660 in the ROI of FIG. 18. The edge portions 640 of the prism in FIG. 17 and the pixel regions 660 of the ROI in FIG. 18 correspond with the peripheral region 510' along the sides of the cigarette in FIG. 19.

Referring now to FIGS. 20 and 21, in the alternative, the prismatic arrangement 500 may comprise one or more triangular prisms 670 and 680 whose form creates a pair of opposing extended pixels regions 660' and 660" in the ROI generated by the processor 52'. In all these alternative embodiments, detection of by-pass regions 24 and other defects along the edges of the end face 10 is facilitated by creating greater separation between the defect and surrounding background pixel regions 520 by the imposition therebetween of a field of pixels which correspond with the peripheral regions 510 and 510'. These arrangements also advantageously extent the inspection processes along the sides of the cigarette so that a greater extent of the cigarette is subject to analysis.

It will be understood that the foregoing is merely illustrative of the principles of the invention, and that various modifications can be made by those skilled in the art without departing from the scope and spirit of the invention. For example, the particular information shown on display 54 can be varied as desired.

What is claimed is:

1. Apparatus for determining whether an end surface of a cigarette has an acceptable appearance, said apparatus comprising:

means for forming an image of said end surface against a contrasting background, said image forming means comprising means for expanding said image to include imaging of a peripheral region along said cigarette adjacent said end surface;

means for digitizing said image as a plurality of pixels, each of said pixels having an initial digital value indicative of the brightness of a corresponding portion of said image;

means for processing said pixels so that each pixel having an initial digital value which has a first polarity relative to a predetermined threshold value is assigned a first of two processed digital values, and so that all other pixels are assigned a second of said two processed digital values, said threshold values being selected so that said background, substantially discolored areas of said end surface and substantially discolored areas of said peripheral region are assigned said first processed digital value and substantially undiscolored areas of said end surface and of said peripheral region are assigned said second processed digital value;

means for identifying as edge pixels those pixels which are adjacent to transitions between pixels having said first and second processed digital values;

means for associating edge pixels which are adjacent to one another so as to identify a boundary of each blob in said image;

means for identifying each blob as a first type of blob or a second type of blob by determining whether each boundary surrounds pixels having said first processed digital value or said second processed digital value, respectively;

means for calculating a characteristic of any blob of at least one of said blob types; and means for determining acceptability of said image by comparing said calculated characteristic to a predetermined value.

2. The apparatus as claimed in claim 1, wherein said means for calculating a characteristic includes means for calculating a size of any blob of said second type and said means for determining acceptability further comprises:

means for determining whether the largest of said calculated size of any blobs of said second type approximately equals a predetermined size.

3. The apparatus as claimed in claim 2, wherein said means for calculating a characteristic includes means for calculating a size of any blob of said first type.

4. The apparatus as claimed in claim 3, further comprising:

means for rejecting said cigarette if said means for determining acceptability determines that said image is an unacceptable image.

5. The apparatus as claimed in claim 1, further comprising:

means for supporting said cigarette during operation of said means for forming an image so that said end surface is spaced from said means for supporting.

6. The apparatus as claimed in claim 5, further comprising:

means for illuminating said end surface so that any light from said means for illuminating which falls on said means for supporting is spaced from said end surface in the image formed by said means for forming an image.

7. The apparatus as claimed in claim 6, wherein said means for forming an image forms said image along a first predetermined axis, and wherein said means for illuminating illuminates said end surface along a second predetermined axis which is inclined relative to said first predetermined axis.

8. The apparatus as claimed in claim 7, wherein said second predetermined axis is inclined relative to said first predetermined axis by an angle of approximately 45°.

9. The apparatus as claimed in claim 7, wherein said first predetermined axis is substantially perpendicular to said end surface.

10. The apparatus as claimed in claim 7, wherein said second predetermined axis is oblique to said end surface.

11. The apparatus as claimed in claim 6, wherein said means for supporting has a surface adjacent to said cigarette which faces in substantially the same direction as said end surface, and wherein said surface of said means for supporting is made so that it visually contrasts with said end surface.

12. The apparatus as claimed in claim 5, wherein said means for supporting moves said cigarette relative to said means for forming an image, and wherein said apparatus further comprises:

means for momentarily illuminating said end surface so that said means for forming an image forms a substantially still image of said end surface.

13. A method of determining whether an end surface of a cigarette has an acceptable appearance, said method comprising the steps of:

forming an image of said end surface and of a peripheral region along said cigarette adjacent said end surface against a contrasting background;

digitizing said image as a plurality of pixels, each of said pixels having an initial digital value indicative of the brightness of a corresponding portion of said image;

processing said pixels so that each pixel having an initial digital value which has a first polarity relative to a predetermined threshold value is assigned a first of two processed digital values, and so that all other pixels are assigned a second of said two processed digital values, said threshold values being selected so that said background and substantially discolored areas of said end surface and said peripheral region are assigned said first processed digital value and substantially undiscolored areas of said end surface and of said peripheral region are assigned said second processed digital value;

identifying as edge pixels those pixels which are adjacent to transitions between pixels having said first and second processed digital values;

associating edge pixels which are adjacent to one another so as to identify a boundary of each blob in said image;

identifying each blob as a first type of blob or a second type of blob by determining whether each boundary surrounds pixels having said first processed digital value or said second processed digital value, respectively;

calculating a characteristic of any blob of at least one of said blob types; and determining acceptability of said image by comparing said calculated characteristic to a predetermined value.

14. The method as claimed in claim 13, wherein said step of calculating a characteristic includes calculating a size of any blob of said second type and said step of determining acceptability further comprises the step of:

determining whether the largest of said calculated size of any blob of said second type approximately equals a predetermined size.

15. The method as claimed in claim 14, wherein said step of calculating a characteristic includes calculating a size of any blob of said first type.

16. The method defined in claim 13, wherein said acceptability determining step includes:

comparing said calculated characteristic of any blob of said first blob type to a first predetermined value; and comparing said calculated characteristic of any blob of said second blob type to a second predetermined value.

17. The method as claimed in claim 16, further comprising the step of:

rejecting said cigarette if said step of determining acceptability determines that said image is an unacceptable image.

18. The method as claimed in claim 16, further comprising the step of:

supporting said cigarette with a support structure during said step of forming an image so that said end surface of said cigarette is spaced from said support structure.

19. The method as claimed in claim 18, further comprising the step of:

illuminating said end surface from a light source so that any light from said light source which falls on said support structure is spaced from said end surface in the image formed in said step of forming an image.

20. The method as claimed in claim 19, wherein said image is formed along a first predetermined axis in said step of forming an image, and wherein in said step of illuminating said end surface said end surface is illuminated along a second predetermined axis which is inclined relative to said first predetermined axis.

21. The method as claimed in claim 20, wherein said second predetermined axis is inclined relative to said first predetermined axis by an angle of approximately 45°.

22. The method as claimed in claim 20, wherein said first predetermined axis is substantially perpendicular to said end surface.

23. The method as claimed in claim 20, wherein said second predetermined axis is oblique to said end surface.

24. The method as claimed in claim 18, wherein said support structure has a surface adjacent to said cigarette which faces in substantially the same direction as said end surface, and wherein said surface of said support structure is made so that it visually contrasts with said end surface.

25. The method as claimed in claim 18, wherein said support structure moves said cigarette relative to said light source, and wherein said method further comprises the steps of:

momentarily illuminating said end surface so that a substantially still image of said end surface is formed during said step of forming an image.

26. The method as claimed in claim 25, wherein said step of momentarily illuminating comprises the step of:

synchronizing the illumination of said end surface with the motion of said support structure.

27. The method as claimed in claim 16, wherein said cigarette is one of a succession of substantially similar objects, wherein said method substantially similarly operates on all of said cigarettes one after another in succession, and wherein said method further comprises the steps of:

displaying the image of a cigarette which is formed in said step of forming an image; and prolonging the display of the image of a cigarette which has been determined to have an unacceptable appearance in said step of determining acceptability so that an operator of the apparatus has additional time to view that image.

28. The apparatus as claimed in claim 1, wherein said means for determining acceptability includes:

means for comparing said calculated characteristic of any blob of said first blob type to a first predetermined value; and means for comparing said calculated characteristic of any blob of said second blob type to a second predetermined value.

29. The apparatus as claimed in claim 11, wherein surfaces of said means for supporting on which light may fall from said means for illuminating are made substantially non-reflective.

30. The apparatus as claimed in claim 11, wherein surfaces of said means for supporting on which light may fall from said means for illuminating are made substantially light-absorbing.

31. The apparatus as claimed in claim 11, wherein said means for supporting comprises a drum on which said cigarette is supported with its longitudinal axis substantially parallel to the longitudinal axis of said drum.

32. The apparatus defined in claim 12, wherein said means for momentarily illuminating comprises:

means for synchronizing the illumination of said end surface with the motion of said means for supporting so that said end surface is illuminated when said end surface is at a predetermined location in the field of view of said means for forming an image.

33. The apparatus defined in claim 1, wherein said cigarette is one of a succession of substantially similar objects, wherein said apparatus substantially similarly operates on all of said cigarettes one after another in succession, and wherein said apparatus further comprises:

means for displaying the image of a cigarette which is formed by said means for forming an image; and means for prolonging the display of the image of a cigarette which has been determined to have an unacceptable appearance by said means for determining whether at least one of said boundaries has a predetermined characteristic so that an operator of the apparatus has additional time to view that image.

34. An apparatus for inspecting an end surface of a cigarette component, comprising:

means for moving a cigarette component along a path, said cigarette component having an end surface;

an image-capturing apparatus at a location along said path, said image-capturing apparatus comprising means for illuminating at least an end portion of said cigarette component at said location, a camera at said location operative so as to capture an image of said end portion of said cigarette component in contrast to a background while said cigarette component is moved through said location, said camera generating an output;

a processor in communication with said camera output, said processor adapted to resolve edge pixels from said camera output, to associate said edge pixels into groups of adjacent edge pixels and to characterize said groups of adjacent edge pixels as to first and second types of blobs;

said image-capturing apparatus further comprising a prism and arranged between said camera and said location so as to be transmissively cooperative with said camera to include within said image of said end portion of said cigarette component a peripheral region along said cigarette component adjacent said end surface, said processor adapted to characterize a group of adjacent edge pixels corresponding to said end surface and said peripheral region as a first one of said first and second types of blobs so as to contrast blobs of both said end surface and said peripheral region from said background.

35. The inspection apparatus as claimed in claim 34 further comprising a rejection station at a second location along said path.

36. The inspection apparatus as claimed in claim 34, wherein said prism comprises a conical prism, with its apex optically directed toward said camera.

37. The inspection apparatus as claimed in claim 34, wherein said a conical prism is in the form of a truncated cone.

38. The inspection apparatus as claimed in claim 34, wherein said prism is semi-spherical.

39. The inspection apparatus as claimed in claim 34, wherein said prism is pyramidal.

40. The inspection apparatus as claimed in claim 34, wherein said prism comprises a triangular prism.

* * * * *